United States Patent [19]

Jahn et al.

[11] Patent Number: 4,844,735
[45] Date of Patent: Jul. 4, 1989

[54] 5-ARYL-CYCLOHEXANE-1-3-DIONE DERIVATIVES, HERBICIDES CONTAINING THESE COMPOUNDS, AND THE PREPARATION OF THESE COMPOUNDS

[75] Inventors: Dieter Jahn, Neckarhausen; Wolfgang Rohr, Wachenheim; Rainer Becker, Bad Durkheim; Bruno Wuerzer, Otterstadt, all of Fed. Rep. of Germany

[73] Assignee: BASF Aktiengesellschaft, Ludwigshafen, Fed. Rep. of Germany

[21] Appl. No.: 178,779

[22] Filed: Apr. 1, 1988

Related U.S. Application Data

[63] Continuation of Ser. No. 732,899, May 9, 1985, abandoned, which is a continuation of Ser. No. 329,125, Dec. 9, 1981, abandoned.

[30] Foreign Application Priority Data

Dec. 19, 1980 [DE] Fed. Rep. of Germany ....... 3047924

[51] Int. Cl.$^4$ ..................... A01N 31/00; C07C 83/00
[52] U.S. Cl. ..................................... 71/121; 564/300
[58] Field of Search ........................... 71/121; 564/300

[56] References Cited

U.S. PATENT DOCUMENTS 3,950,420  4/1976  Sawaki et al. ..................... 564/300

FOREIGN PATENT DOCUMENTS 2439104  3/1975  Fed. Rep. of Germany ...... 264/453

OTHER PUBLICATIONS

Chem. Abstracts, vol. 85, Nr. 5281g (1976);
Chem. Abstracts, vol. 86, Nr. 16357h (1977).
Proc. 4th International Congress of Pesticide Chemistry (IUPAC), 1978, p. 235.

Primary Examiner—Robert V. Hines
Attorney, Agent, or Firm—Keil & Weinkauf

[57] ABSTRACT

Compounds of the general formula

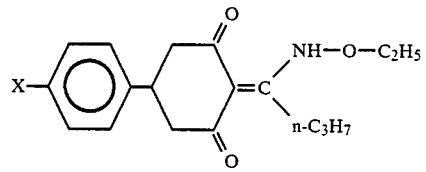

where X is fluorine, chlorine, ethyl or n-propyl, and the salts of these compounds, and herbicides containing the compounds or their salts.

5 Claims, No Drawings

5-ARYL-CYCLOHEXANE-1-3-DIONE DERIVATIVES, HERBICIDES CONTAINING THESE COMPOUNDS, AND THE PREPARATION OF THESE COMPOUNDS

This application is a continuation of Ser. No. 732,899, filed May 9, 1985 which is a continuation of Ser. No. 329,125, filed Dec. 9, 1981, both now abandoned.

The present invention relates to novel 5-arylcyclohexane-1,3-dione derivatives and to herbicides containing these compounds.

It is known that 5-aryl-cyclohexane-1,3-dione derivatives can be used for the selective control of undesirable grasses in broad-leaved crops (German Published Application DAS No. 2,439,104). It is also known that, in particular, p-substitution of the phenyl ring causes the active ingredient to be tolerated by the grassy crop plant wheat (Proc. 4th International Congress of Pesticide Chemistry (IUPAC), 1978, page 235). The best results have been achieved with compounds containing a p-methyl radical, such as 2-(1-ethoxyaminopropylidene)-5-(4-methylphenyl)-cyclohexane-1,3-dione. In the above publication, the observation that changing the alkoxyaminopropylidene radical to alkoxyaminobutylidene leads both to a drop in herbicidal activity and to a reduction in the toleration by crops is particularly noteworthy. In the example using wheat as the crop, only 5-aryl-cyclohexane-1,3-dione derivatives containing ethoxyaminopropylidene radicals are mentioned as active ingredients which cause little damage to wheat.

We have found that compounds of the general formula

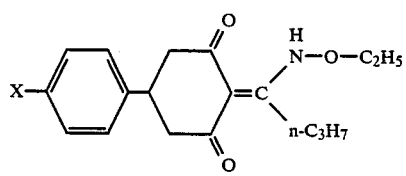

where X is fluorine, chlorine, ethyl or n-propyl, and the salts of these compounds, control undesirable grasses well in cereals, if X is ethyl, and are, surprisingly, better tolerated by wheat and barley than the known active ingredient, whilst if X is fluorine or chlorine, they still have a good herbicidal action on Alopercurus myosuroides and other undesirable grasses, with a certain reduction in action on Avena fatua, and are likewise surprisingly well tolerated by cereals.

The novel compounds can exist in several tautomeric forms:

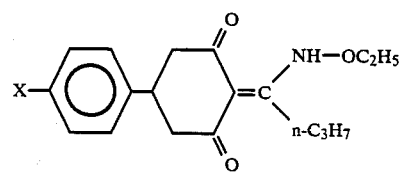

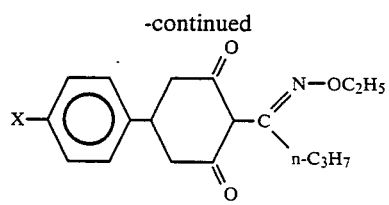

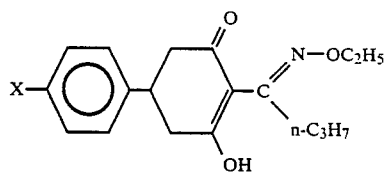

All these forms are embraced by the claim.

The novel compounds can be prepared from the ketones of the general formula I, in accordance with the following equation:

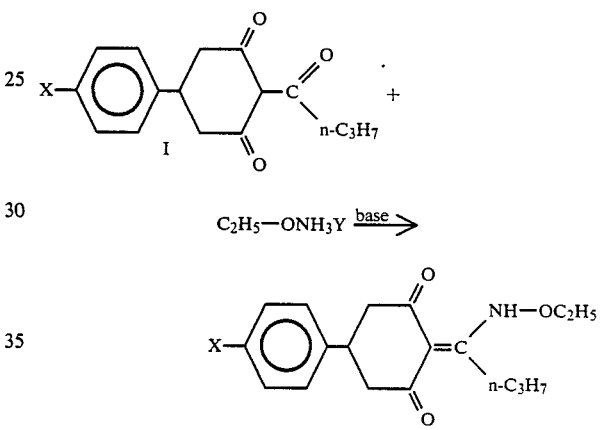

where X has the above meanings and Y is an anion, for example chloride, sulfate, nitrate or bromide.

The reaction is advantageously carried out in a heterogeneous phase system in an inert solvent at from 0 to 80° C., or from 0° to the boiling point of the mixture, in the presence of a base, for example ammonia or a carbonate, bicarbonate, acetate, alcoholate, hydroxide or oxide of an alkali metal or an alkaline earth metal, in particular of sodium, potassium, magnesium or calcium. Organic bases, such as pyridine or tertiary amines, can also be used.

A defined pH range which is particularly suitable for the reaction is that from pH 2 to pH 7, in particular from pH 4.5 to pH 5.5. This pH is advantageously established by adding acetates, for example alkali metal acetates, especially sodium acetate or potassium acetate, or their mixtures. The alkali metal acetates are use, for example, in amounts of from 0.5 to 2 moles per mole of the ammonium compound.

Suitable solvents are, for example, methanol, ethanol, isopropanol, benzene, tetrahydrofuran, chloroform, acetonitrile, dichloroethane, ethyl acetate, dioxane and dimethylsulfoxide.

The reaction takes some hours. The reaction produce can be isolated by concentrating the mixture, adding water and extracting the mixture with a nonpolar solvent, or by distilling off the solvent under reduced pressure.

The novel compounds can also be prepared by reacting the compounds I with ethoxyamine.

The compounds of the formula I can be obtained by acylating the substituted cyclohexane-1,3-diones II

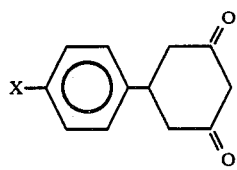

as described, for example, in Tetrahedron Lett. 29, 2491.

Compounds for the formula II can also exist in the following tautomeric form IIa

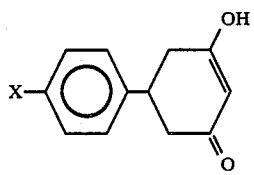

Compounds of the formula II can be obtained from the esters III or their salts by boiling with an alkali metal hydroxide solution and subsequent heating in an acid medium.

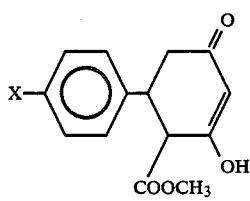

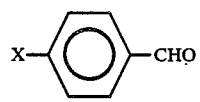

Compounds of the formula III can be prepared from benzaldehydes by methods which are known from the literature, for example by aldol condensation with acetone and subsequent cyclization with malonates, by a method similar to that in Organic Synthesis Coll. Vol. II, page 200. The compounds of the formula III are also obtained by reacting the aldehyde

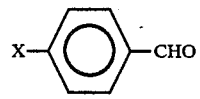

with malonic acid by the method of Knoevenagel-Doebner (of. Org. Reactions, Volume 15, page 204), esterifying the acid formed and cyclizing the product with an acetoacetate by a method similar to that described, for example, in Houben-Weyl, Methoden der Organischen Chemie, Volume 8, page 598.

Examples of salts of the compounds are the alkali metal salts, in particular the potassium and sodium salts.

The sodium and potassium salts of the novel compounds can be obtained by treating these compounds with sodium hydroxide or potassium hydroxide in aqueous solution or in an organic solvent, such as methanol, ethanol or acetone.

Sodium alcoholates and potassium alcoholates can also be used as the base.

Other metal salts, for example the manganese, copper, zinc, iron and barium salts, can be prepared from the sodium salt by reaction with the corresponding metal chlorides in aqueous solution.

The Examples which follow illustrate the preparation of the novel cyclohexane-1,3-diones.

In the Examples, parts by weight bear the same relation to parts by volume as that of the kilogram to the liter.

EXAMPLE 1

20.1 parts by weight of 2-butyryl-5-(4-fluorophenyl)-cyclohexane-1,3-dione, 7.1 parts by weight of ethoxyammonium chloride, 6.6 parts by weight of anhydrous sodium acetate and 120 parts by volume of ethanol are stirred at room temperature for 16 hours. The solvent is then distilled off under reduced pressure, the residue is stirred with 100 parts by volume of water and 100 parts by volume of methylene chloride, the organic phase is separated off and the aqueous phase is extracted with 50 parts by volume of methylene chloride. The combined organic phases are washed with water, dried over sodium sulfate and concentrated under reduced pressure. 2-(Ethoxyaminobutylidene)-5-(4-fluorophenyl)-cyclohexane-1,3-dione is obtained as a solid having the following structural formula (active ingredient No. 1):

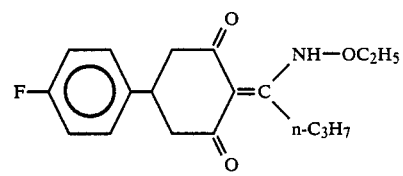

Recrystallization from cyclohexane gives white crystals of melting point 58°–59° C.

$C_{18}H_{22}NO_3F$ (molecular weight: 319):
calculated: C,67.69; H,6.94; N,4.39;
found: C,67.7; H,6.9; N,4.3.

EXAMPLE 2

13.5 parts of 2-butyryl-5-(4-chlorophenyl)-cyclohexane-1,3-dione, 4.5 parts by weight of ethoxyammonium chloride, 4.5 parts by weight of anhydrous sodium acetate and 100 parts by volume of ethanol are reacted, and the mixture is worked up, in a manner similar to that in Example 1. 2-(Ethoxyaminobutylidene)-5-(4-chlorophenyl)-cyclohexane-1,3-dione is obtained as a solid, which is recrystallized from cyclohexane. The product has a melting point of 77° C. (active ingredient No. 2)

$C_{18}H_{22}NO_3Cl$ (molecular weight: 336)
calculated: C,64.38; H,6.60; N,4.17;
found: C,64.1; H,6.4; N,3.9.

EXAMPLE 3

28.6 parts by weight of 2-butyryl-5-(4-ethylphenyl)-cyclohexane-1,3-dione and 6.1 parts by weight of ethoxyamine are stirred in 150 parts by volume of ethanol at room temperature for 8 hours. The mixture is concentrated under reduced pressure, the residue is taken up in 200 parts by volume of methylene chloride and the solution is washed with 5% strength aqueous hydrochloric acid and water dried over sodium sulfate and concentrated under reduced pressure. 2-(Ethoxyaminobutylidene)-5-(4-ethylphenyl)-cyclohexane-1,3-dione is obtained as an oil (active ingredient No. 3).

$n_D^{23}$: 1.5448.

$C_{20}H_{27}NO_3$ (329):

calculated: C,72.92; H,8.26; N,4.25;

found: C,72.2; H,8.2; N,4.5.

EXAMPLE 4

15.0 parts by weight of 2-butyryl-5-(4-n-propylphenyl)-cyclohexane-1,3-dione is reacted with 5.1 parts by weight of ethoxyammonium chloride and 4.5 parts by weight of anhydroud sodium acetate in 120 parts by volume of ethanol, and worked up as in Example 1. There is obtained 2-(ethoxyaminobutylidene)-5-(4-n-propylphenyl)-cyclohexane-1,3-dione (active ingredient No. 4).

$n_D^{24}$ :1.5452.

Application may be effected for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used.

For the preparation of solutions, emulsions, pastes and oil dispersions to be sprayed direct, mineral oil fractions of medium to high boiling point, such as kerosene or diesel oil, further coal-tar oils, and oils of vegetables or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnapohthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol gylcol ethers, condensation products of sulfonated naphthalene and naphthalene derivatives with formaldehyde, condensation products of naphthalene or naphthalenesulfonic acids with phenol and formaldehyde, polyoxyethylene octylphenol ehters, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated caster oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agent may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicatse, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably from 0.5 to 90, wt% of active ingredient.

The active ingredients are applied, for instance by watering, scattering, dusting, spraying or atomizing, to the plants or soil, by coating plants, or by introducing them into the irrigation water.

EXAMPLE I 90 parts by weight of compound 1 is mixed with 10 parts by weight of N-methyl-$\beta$-pyrrolidone. A mixture is obtained which is suitable for application in the form of very fine drops.

EXAMPLE II 10 parts by weight of compound 2 is dissolved in a mixture consisting of 90 parts by weight of xylene, 6 parts by weight of the adduct of 8 to 10 moles of ehtylene oxide with 1 mole of oleic acid-N-monoethanolamide, 2 parts by weight of the calcium salt of dodecylbenzenesulfonic acid, and 2 parts by weight of the adduct of 40 moles of ethylene oxide with 1 mole of caster oil. By pouring the solution into water and uniformly distributing it therein, an aqueous dispersion is obtained.

EXAMPLE III 20 parts by weight of compound 2 is dissolved in a mixture consisting of 40 parts by weight of cyclohexane, 30 parts by weight of isobutanol, 20 pats by weight of the adduct of 7 moles of ehtylene oxide with 1 mole of isooctylphenol, and 10 parts by weight of the adduct of 40 moles of ethylene oxide with 1 mole of caster oil. By pouring the solution into water and finely distributing it therein, an aqueous dispersion is obtained.

EXAMPLE IV 20 parts by weight of compound 3 is dissolved in a mixture consisting of 25 parts by weight of cyclohexanol, 65 parts by weight of a mineral oil fraction having a boiling point between 210° and 280°C., and 10 parts by weight of the adduct of 40 moles of ethylene oxide with 1 mole of castor oil. By pouring the solution into water and uniformly distributing it therein, an aqueous dispersion is obtained.

EXAMPLE V 80 parts by weight of compound 1 is well mixed with 3 parts by weight of the sodium salt of diisobutylnaphthalene-$\alpha$-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

EXAMPLE VI 5 parts by weight of compound 1 is intimately mixed with 95 parts by weight of particulate kaolin. A dust is obtained containing 5% by weight of the active ingredient.

EXAMPLE VII 30 parts by weight of compound 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE VIII 40 parts by weight of compound 1 is intimately mixed with 10 parts of the sodium salt of a phenolsulfonic acid-urea-formaldehyde condensate 2, parts of silica gel and 48 parts of water to give a stable, aqueous dispersion. Dilution in water gives an aqueous dispersion.

EXAMPLE IX 20 parts by compound 1 is initimately mixed with 12 parts of the calcium salt of dodecylbenzenesulfonic acid, 8 parts of a fatty alcohl polyglycol ether, 2 parts of the sodium salt of a phenosulfonic acid-urea-formaldehyde condensate and 68 parts of a paraffinic mineral oil. A stable oily dispersion is obtained.

The active ingredients may be applied either pre- or post- emergence.

The amounts of active ingredient applied depend on the season of the year and the growth stage, and vary from 0.1 to 15 kg/ha and more.

The influence of the novel 5-aryl-cyclohexane-1,3-dione derivatives on the growth of grass crops and unwanted grass species is demonstrated in greenhouse experiments.

The vessels employed were plastic flowerpots having volume of 300 cm$^3$ and which were filled with a loamy sand containing about 1.5% humus. The seeds of the plants listed in Table 1 were sown shallow, and separately, according to species. For the postemergence treatment described here, the test plants were grown to a height of from 5 to 15 cm, depending on growth shape. The active ingredients were then applied, for example at rates of 0.25 kg/ha and 1.0 kg/ha, and, in the case of one active ingredient, only at 1.0 kg/ha. The active ingredients were suspended or emulsified in water as vehicle, and sprayed through finely distributing nozzles.

The agent used for comparison purposes was

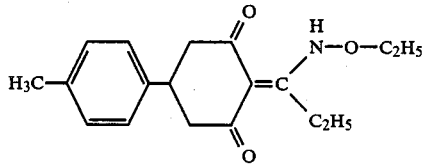

A which is disclosed in German Printed Application DE-AS 24 39 104 and is stated in the literature to be particularly selective and effective.

The experiments were carried out in the greenhouse. They were run for from 2 to 4 weeks. During this period, the plants were tended and their reaction to the various treatments was assessed on a 0 to 100 scale, 0 denoting no damage or normal emergence, and 100 denoting nonemergence or complete destruction of at least the visible shoot parts.

The results show that the novel compounds are suitable for selective control of unwanted grasses in cereals, and that they are surprisingly well tolerated. However, there seem to be differences in compatibility between various cereal species. In investigations into the herbicidal action on postemergence application of 0.25 and 1.0 kg/ha of active ingredient in the greenhouse, novel compound no. 3 has a herbicidal action which is only slightly weaker than that of comparative agent A, but it is, however, tolerated to a much greater extent by the cereal species barley and wheat.

Active ingredient no. 1 also had a useful action on unwanted grasses and was better tolerated by cereals than comparative agent A.

Further, new compound no. 2, applied postemergence in the greenhouse at a rate of 1.0 kg/ha, had an acceptable action on Alopecurus myosuroides, and was much better tolerated by barley and wheat than comparative agent A.

In further greenhouse experiments carried out in accordance with the methods described above, compound no. 3 exhibited, when applied postemergence at 0.5 kg/ha, herbicidal action on unwanted grasses which is slightly weaker than that of comparative agent A. However, the cereal species rye tolerates compound no. 3 much better than comparative agent A, thus giving the former superior utility.

All the novel compounds listed herein also have an appreciable herbicidal action when applied preemergence.

In addition to cereal species, the novel compounds also have a seletive herbicidal action in broadleaved crops.

If certain crop plants tolerate the active ingredients less well, application techniques may be used in which the agents are sprayed from suitable equipment in such a manner that the leaves of sensitive crop plants are if possible not touched, and the agents reach the soil or the unwanted plants growing beneath the crop plants (post-directed, lay-by treatment).

In view of the good tolerance of the active ingredients and the many application methods possible, the agents according to the invention, or mixtures containing them, may be used in a range of crops for removing unwanted plants.

The following crop plants may be mentioned by way of example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rape seed |

| Botanical name | Common name |
| --- | --- |
| Brassica napus var. napobrassica | |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) Sorghum dochna | sorghum |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

We claim:
1. A compound of the formula

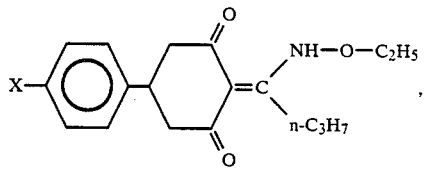

where X is ethyl.

2. A process for combating unwanted grasses among crop plants, wherein the grasses or the soil in which the crops are planted is treated with an effective amount of a 5-aryl-cyclohexane-1,3-dione derivative of the formula

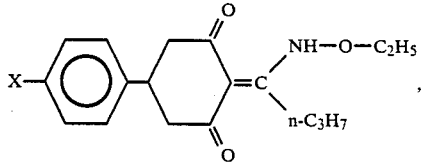

where X is ethyl.

3. A process as defined in claim 2, wherein a peremergence application of the 5-aryl-cyclohexane-1,3-dione derivative is applied to the soil in which the crops are planted.

4. A process as defined in claim 2, wherein the crop plants are broadleaved plant.

5. A process as defined in claim 2, wherein the crop plants are wheat or barley.

* * * * *